United States Patent [19]

Higashiguthi et al.

[11] 4,362,871
[45] Dec. 7, 1982

[54] POLYCARBOXYLIC ACID GLYCIDYL ESTERS AND PROCESS FOR PREPARING THE SAME

[75] Inventors: Teruaki Higashiguthi, Kashiwara; Mithio Ishioka, Nara, both of Japan

[73] Assignee: Okamura Oil Mill Limited, Japan

[21] Appl. No.: 199,281

[22] Filed: Oct. 21, 1980

[30] Foreign Application Priority Data

Oct. 26, 1979 [JP] Japan .................. 54-138935

[51] Int. Cl.³ .................. C07D 303/27; C07D 303/16
[52] U.S. Cl. ...................................... 542/427; 549/562
[58] Field of Search ............ 260/348.13, 348.59, 260/348.61; 542/427

[56] References Cited

U.S. PATENT DOCUMENTS

| | | | |
|---|---|---|---|
| 2,772,296 | 11/1956 | Mueller | 260/348.13 |
| 2,940,986 | 6/1960 | Newey | 260/348.59 |
| 3,057,809 | 10/1962 | Newey | 260/348.59 X |
| 3,075,999 | 1/1963 | June et al. | 260/348.13 |
| 3,644,431 | 2/1972 | Heer et al. | 260/348.59 |
| 4,859,314 | 1/1975 | Dukes et al. | 260/348.59 |

*Primary Examiner*—Earl A. Nielsen
*Attorney, Agent, or Firm*—Larson and Taylor

[57] ABSTRACT

A polycarboxylic acid glycidyl ester represented by the formula

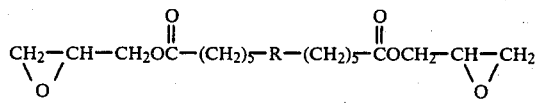

wherein $-R-$ is $-(CH_2)_8-$, -continued $-CH_2-CH=CH-(CH_2)_2-CH=CH-CH_2-$, $$-\underset{\underset{CH=CH_2}{|}}{CH}-(CH_2)_2-CH=CH-CH_2-,$$

$$-CH_2-\underset{\underset{CH_3}{|}}{\overset{CH_3}{|}}{C}=CH-(CH_2)_2-CH=\overset{CH_3}{\underset{|}{C}}-CH_2-,$$

$$-CH_2-\underset{\underset{CH_3}{|}}{CH}-(CH_2)_4-\overset{CH_3}{\underset{|}{CH}}-CH_2-,$$

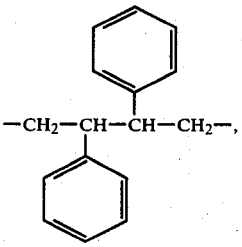

$$-\underset{\underset{COOR'}{|}}{CH}-\underset{\underset{COOR'}{|}}{CH}-\underset{\underset{}{|}}{\overset{COOR'}{|}}{CH}-\underset{\underset{}{|}}{\overset{COOR'}{|}}{CH}-,$$

$$-CH_2-\underset{\underset{COOR'}{|}}{\overset{CH_3}{|}}{C}-\underset{\underset{CH_3}{|}}{\overset{COOR'}{|}}{C}-CH_2-\text{ or}$$

$$-CH_2-\underset{\underset{COOR'}{|}}{CH}-\overset{COOR'}{\underset{|}{CH}}-CH_2-, \text{ and } R' \text{ is } -CH_2-\underset{\underset{O}{\diagdown/}}{CH}-CH_2.$$

5 Claims, No Drawings

POLYCARBOXYLIC ACID GLYCIDYL ESTERS AND PROCESS FOR PREPARING THE SAME

This invention relates to novel polycarboxylic acid glycidyl esters and to a process for preparing the esters.

The polycarboxylic acid glycidyl esters of this invention are novel compounds which have not been disclosed in literature and are represented by the formula (I)

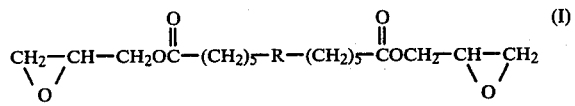   (I)

wherein R is $-(CH_2)_8-$,

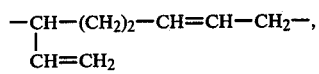

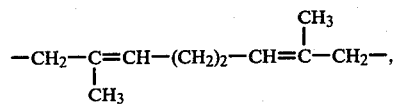

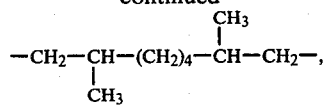

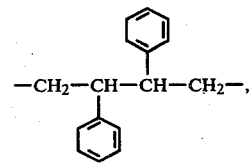

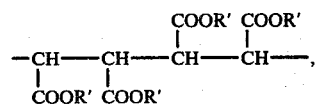

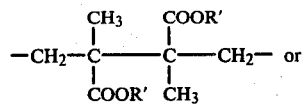

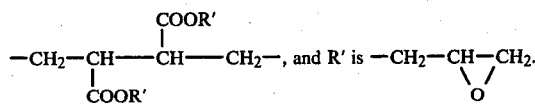, and R' is $-CH_2-CH-CH_2$ with epoxide.

Examples of polycarboxylic acid glycidyl esters of the formula (I) are listed in Table 1 below.

TABLE 1

1. Octadecane-1,18-dicarboxylic acid diglycidyl ester (Compound 1)

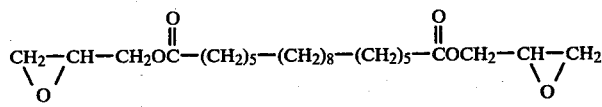

2. 7,11-Octadecadiene-1,18-dicarboxylic acid diglycidyl ester (Compound 2)

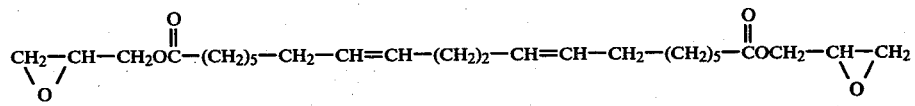

3. 6-Vinyl-9-hexadecene-1,16-dicarboxylic acid diglycidyl ester (Compound 3)

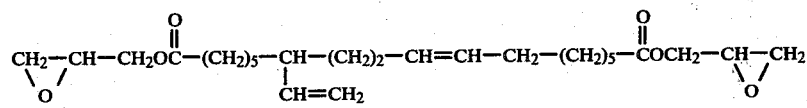

4. 7,12-dimethyl-7,11-octadecadiene-1,18-dicarboxylic acid diglycidyl ester (Compound 4)

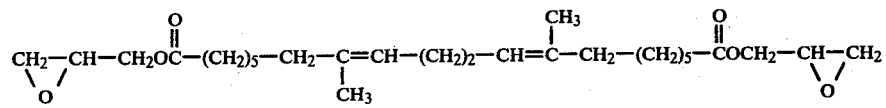

5. 7,12-Dimethyl-octadecane-1,18-dicarboxylic acid diglycidyl ester (Compound 5)

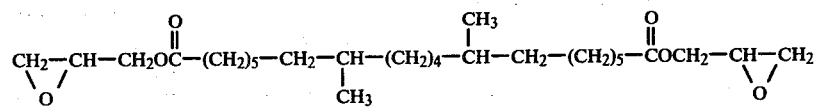

6. 7,8-Diphenyl-tetradecane-1,14-dicarboxylic acid diglycidyl ester (Compound 6)

TABLE 1-continued

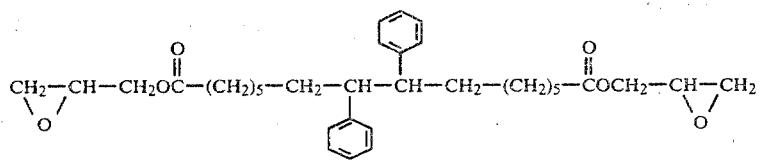

7. Tetradecane-1,6,7,8,9,14-hexacarboxylic acid hexaglycidyl ester (Compound 7)

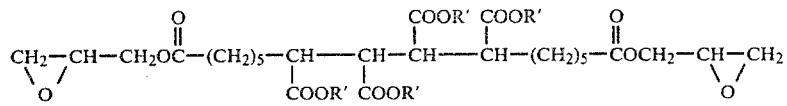

wherein R' is —CH$_2$—CH—CH$_2$.
              \ /
               O 8. 7,8-Dimethyl-tetradecane-1,7,8,14-tetracarboxylic acid tetraglycidyl ester (Compound 8)

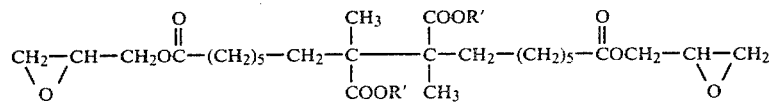

wherein R' is —CH$_2$—CH—CH$_2$.
              \ /
               O

9. Tetradecane-1,7,8,14-tetracarboxylic acid tetraglycidyl ester (Compound 9)

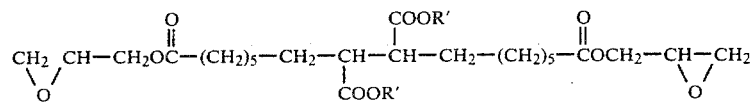

wherein R' is —CH$_2$—CH—CH$_2$.
              \ /
               O

The polycarboxylic acid glycidyl esters of the formula (I) can be prepared by various methods, preferably, for example, by reacting a polycarboxylic acid of the formula (II) below with epichlorohydrin.

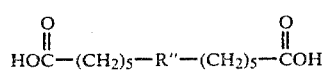
(II)

wherein —R″ is —(CH$_2$)$_8$—,

—CH$_2$—CH=CH—(CH$_2$)$_2$—CH=CH—CH$_2$—,

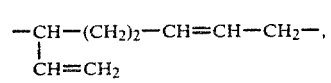

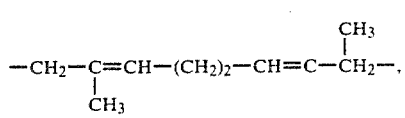

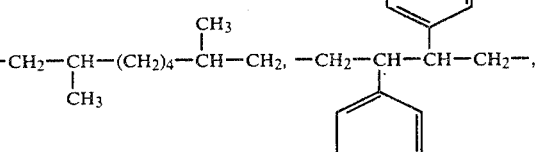

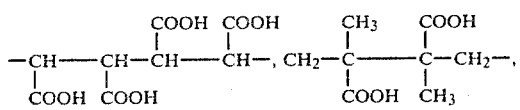

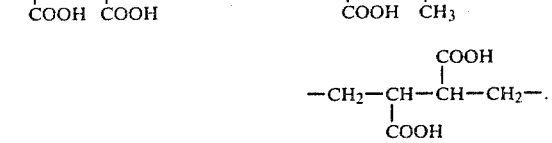

Examples of polycarboxylic acids represented by the formula (II) and useful as materials for preparing the polycarboxylic acid glycidyl esters (I) are shown in Table 2.

TABLE 2

1. Octadecane-1,18-dicarboxylic acid (Material Compound 1)

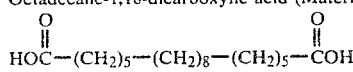

TABLE 2-continued 2. 7,11-Octadecadiene-1,18-dicarboxylic acid (Material Compound 2)

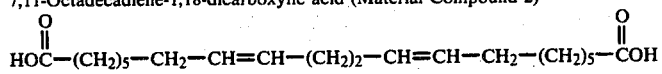

3. 6-Vinyl-9-hexadecene-1,16-decarboxylic acid (Material Compound 3)

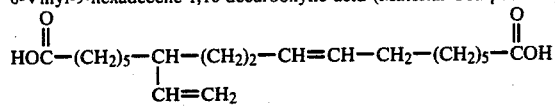

4. 7,12-Dimethyl-7,11-octadecadiene-1,18-dicarboxylic acid (Material Compound 4)

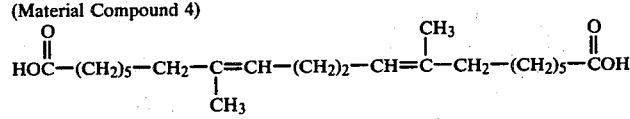

5. 7,12-Dimethyl-octadecane-1,18-dicarboxylic acid (Material Compound 5)

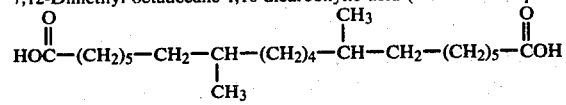

6. 7,8-Diphenyl-tetradecane-1,14-dicarboxylic acid (Material Compound 6)

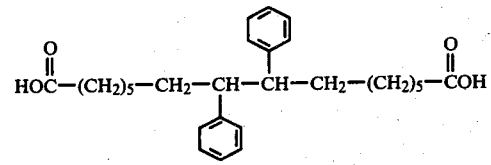

7. Tetradecane-1,6,7,8,9,14-hexacarboxylic acid (Material Compound 7)

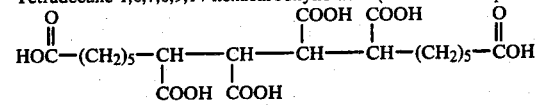

8. 7,8-Dimethyl-tetradecane-1,7,8,14-tetracarboxylic acid (Material Compound 8)

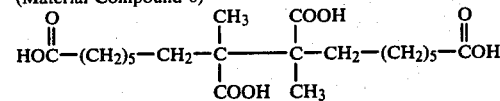

9. Tetradecane-1,7,8,14-tetracarboxylic acid (Material Compound 9)

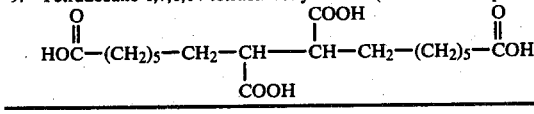

Of these polycarboxylic acids of the formula (II) useful as materials, Material Compounds 1 to 5 are known, while Material Compounds 6 to 9 are novel.

Material Compound 6 is prepared by reacting cyclohexanone with hydrogen peroxide in an alcohol in the presence of an acid catalyst to form an alkoxycyclohexanol peroxide, reacting the peroxide with styrene in the presence of a ferrous salt to obtain a polycarboxylic acid ester, and hydrolyzing the ester.

For the reaction between cyclohexanone and hydrogen peroxide, usually 0.5 to 2 moles, preferably 1 mole, of the latter is used per mole of the former. Useful acid catalysts are inorganic acids, such as sulfuric acid, phosphoric acid, hydrochloric acid, etc., among which sulfuric acid is preferable. The acid catalyst is used in an amount of 0.5 to 10 parts (by weight, the same as hereinafter), preferably 1 to 2 parts, per 100 parts of cyclohexanone. Useful alcohols are usually lower alcohols, preferred examples of which are methanol, ethanol, propanol, isopropanol, n-butanol, tert-butanol, etc. Usually about 200 to about 1,000 parts, preferably about 400 to about 600 parts, of such alcohol is used per 100 parts of cyclohexanone. The reaction is conducted usually at −30° to 30° C., preferably −5° to 5° C., for 5 to 60 minutes, preferably about 10 to about 20 minutes.

The alkoxycyclohexanol peroxide thus formed is reacted with styrene in the ratio of 1 to 3 moles, preferably about 1.2 to about 2.0 moles, of the latter per mole of the former, in the presence of a ferrous salt. For this reaction, various ferrous salts are useful, including, for example, ferrous sulfate, ferrous chloride, ferrous acetate, ammonium salt of ferrous sulfate, etc. Usually about 1 to about 2 moles, preferably about 1.2 to about 2.0 moles, of such ferrous salt is used per mole of the alkoxycyclohexanol peroxide. The reaction is conducted usually at −10° to 10° C., preferably −5° to 5° C., for about 0.5 to about 1 hour. A solvent, although not always needed, is usable. Examples of useful solvents are lower alcohols, such as methyl alcohol, ethyl alcohol, n-propyl alcohol, n-butyl alcohol, tert-butyl alcohol, etc. In this way, Material Compound 6 is prepared in the form of an ester. The ester is hydrolyzed to obtain Material Compound 6 in a usual manner, for example, by adding an alkali metal hydroxide to the ester while heating and stirring the ester with water in an amount about 1 to 2 times the amount by weight of the ester, and admixing sulfuric acid or like mineral acid.

Material Compound 7 can be prepared in the same manner as Material Compound 6 with the exception of using a maleic acid ester in place of styrene. Useful maleic acid esters are lower alkyl mono- or diesters of maleic acid, especially lower alkyl diesters of maleic acid. Exemplary of such esters are dimethyl maleate, diethyl maleate, di-n-propyl maleate, di-n-butyl maleate, di-tert-butyl maleate, etc.

Material Compound 8 can be prepared in the same manner as Material Compound 6 except that a methacrylic acid ester is used in place of styrene. Material Compound 9 is prepared similarly with the use of an acrylic acid ester in place of styrene. Useful methacrylic acid esters are lower alkyl esters of methacrylic acid, such as methyl methacrylate, ethyl methacrylate, n-propyl methacrylate, n-butyl methacrylate, tert-butyl methacrylate, etc. Useful acrylic acid esters are lower alkyl esters of acrylic acid, such as methyl acrylate, ethyl acrylate, n-propyl acrylate, n-butyl acrylate, tert-butyl acrylate, etc.

Material Compounds 1 to 5, which are known compounds, can be prepared by various known processes. Typically material Compounds 1 to 5 are prepared by the following process.

To prepare Material Compounds 2 and 3, the same procedure as in the preparation of Material Compound 6 is repeated with the exception of using butadiene in place of the styrene, whereby a mixture of Material Compounds 2 and 3 is obtained. Then the mixture is separated in the usual manner into individual compounds, i.e. Material Compounds 2 and 3.

Material Compound 1 is prepared by hydrogenating Material Compound 2 in the usual manner.

The same procedure as in the preparation of Material Compound 6 is repeated with the exception of using isoprene in lieu of styrene to obtain a mixture of Material Compound 4 and Material Compound 5, the latter not being hydrogenated. Then the mixture is separated in the usual manner into Material Compound 4 and Material Compound 5 not being hydrogenated. The latter is hydrogenated in the usual manner to produce Material Compound 5.

The polycarboxylic acid represented by the formula (II) and serving as the starting material is reacted with epichlorohydrin in accordance with a usual process for reacting a carboxylic acid with epichlorohydrin. Typically, for example, the polycarboxylic acid of the formula (II) is reacted with epichlorohydrin using at least one of tertiary amines and quaternary ammonium salts as a catalyst. Tertiary amines and quaternary ammonium salts heretofore used are usable. Examples of useful tertiary amines are triethylamine, tri-n-propylamine, benzyldimethylamine, triethanolamine, etc. Exemplary of useful quaternary ammonium salts are ammonium tetramethylhydroxide, ammonium benzyltrimethylhydroxide, benzyltrimethyl ammonium chloride, benzyltriethyl ammonium chloride, benzyltrimethyl ammonium acetate, methyltriethyl ammonium chloride, etc.

The catalyst is used in an amount usually of 0.02 to 1.0% by weight, preferably 0.1 to 0.3% by weight, based on the combined amount of the polycarboxylic acid and epichlorohydrin. The reaction is conducted usually at 80° to 150° C., preferably about 90° to 110° C. for about 0.5 to about 1 hour.

The reaction mixture is then neutralized with an alkali hydroxide, such as sodium hydroxide or potassium hydroxide, followed by the removal of hydrochloric acid in the usual manner, whereby a polycarboxylic acid glycidyl ester of the formula (I) can be obtained. The desired compound can be isolated and purified by a usual method, for example, by filtration, solvent extraction, washing, distillation or recrystallization.

Given below is a preferred mode of reacting the polycarboxylic acid of the formula (II) with epichlorohydrin. The polycarboxylic acid of the formula (II) is admixed with epichlorohydrin in an amount of 3 to 10 moles per carboxyl group of the acid. Subsequently a tertiary amine, quaternary ammonium salt or like catalyst is added to the mixture. The resulting mixture is subjected to addition reaction at 80° to 110° C. as a first step to obtain the corresponding chlorohydrin ester of carboxylic acid. When the neutralization value has reduced to not higher than 1, the reaction is discontinued. As a second step, a concentrated aqueous solution of alkali hydroxide (concentration: 40 to 60%) in 5 to 30% excess of the theoretical amount is immediately thereafter added in small portions to the reaction mixture for the removal of hydrochloric acid, and the water added and the water formed are removed as an azeotropic mixture of water and epichlorohydrin. After the dropwise addition of the alkali hydroxide, the reaction mixture is heated very rapidly to 105° C., whereupon the reaction is discontinued by quickly cooling the mixture to room temperature. The precipitate of sodium chloride is filtered off. After recovering the epichlorohydrin from the filtrate in a vacuum, the product was dissolved in an inert organic solvent, and the solution was washed with water to remove the catalyst and a trace of sodium chloride. The solution is then heated to about 140° C. in a vacuum for the recovery of the inert organic solvent, affording the desired compound of this invention.

The novel polycarboxylic acid glycidyl esters of this invention have the following usefulness.

Compound 1 is solid at room temperature and is very useful as an epoxy resin for powder coating compositions. Whereas conventional powder coating compositions incorporating conventional bisphenol A type epoxy resin have the most serious drawback of chalking, those containing Compound 1 as an epoxy resin have greatly improved resistance to chalking and remain free of any chalking, for example, when exposed to outdoor atmosphere for one year. Powder coating compositions can be formulated with use of Compound 1 in the same manner as conventional epoxy resin-containing powder coating compositions except that the compound is used in place of, or conjointly with, the conventional epoxy resin. For example, Compound 1 or a mixture of Compound 1 and a conventional epoxy resin is kneaded with a curing agent, pigment and other desired additives with heating, and the mixture is cooled and thereafter pulverized. Useful curing agents, pigments and other additives are those heretofore used. Examples of useful curing agents are dicyandiamide, boron fluorideamine complex salt, dibasic acid hydrazides, m-phenylenediamine, 4,4'-methylenedianiline, 4,4'-diaminodiphenylsulfone, acid anhydrides such as trimellitic anhydride, methyltetrahydrophthalic anhydride, benzophenonetetracarboxylic anhydride, pyromellitic anhydride, etc., and imidazole curing agents, among which dicyandiamide, dibasic acid hydrazides and acid anhydrides are preferable. Examples of useful pigments are coloring pigments, such as titanium white, carbon black, molybdenum red, chrome yellow, chromium oxide, ultramarine, azo pigments, and extender pigments, such as calcium carbonate, clay, talc, etc. Examples of other useful additives are "Aerosil" and like flow regulating agents, glass fiber and like reinforcing agent, silicon and like levelling agents, thickening agents, fillers, etc. The amounts of such curing agents, pigments and other additives to be used are not particularly limited but are suitably determined in accordance with the components and use of the coating composition. For example, the curing agent is used approximately in stoichiometrically the same amount as the combined epoxy equivalent weight of the epoxy resins used.

Compounds 2 to 9 are all liquid and have viscosities of up to 200 cps at room temperature and are advantageously usable for imparting flexibility to epoxy resins when reacted therewith. Conventional epoxy resins, when cured, generally have low flexibility, which is usually increased with use of a flexibility imparting agent. In addition to being capable of giving flexibility to epoxy resins on curing, such agent must fulfill the requirements of being miscible with epoxy resins, having high storage stability when admixed therewith, causing no shrinkage to epoxy resins on curing, and not impairing the properties of the cured product obtained, for example, in respect of mechanical strength, resistance to thermal impact, chemical stability, electrical characteristics, etc. Compounds 2 to 9 of this invention all satisfy these requirements. Stated more specifically, these compounds are highly miscible with epoxy resins and can be mixed with an epoxy resin in any ratio, affording a mixture having an exceedingly high storage stability at low temperatures. When stored, for example, at 0° C. for a long period of time, such mixture will not produce any crystals, nor will it separate into phases. The mixture is curable without entailing any shrinkage or deformation, giving a product which is outstanding in mechanical strength, electrical characteristics, resistance to chemicals as well as to heat, and bond strength.

The use of Compounds 2 to 9 as flexibility imparting agents will be described below in greater detail.

These novel compounds of this invention can be admixed with a wide variety of epoxy resins heretofore known. Typical of such resins are bisphenol A type epoxy resins (e.g. "EPIKOTE," trade mark, product of Shell Co.) The amount of the present compounds to be admixed with such epoxy resin is not particularly limited but is widely variable. Usually 5 to 400 parts, preferably about 10 to about 150 parts, of the compound is used per 100 parts of the epoxy resin. When used in lesser amounts, the compounds fail to give sufficient flexibility to the cured product, whereas when they are used in exceedingly large amounts, there is the tendency that the cured product will have a reduced heat-resistance.

Curing agents can be incorporated into compositions of a compound of this invention and a conventional epoxy resin. A wide variety of curing agents are usable in varying amounts. Usually curing agents are used approximately in stoichiometrically the same amount as the combined epoxy equivalent weight of the epoxy resin and the present compound. Furthermore, curing accelerators, extenders, plasticizers and various other additives can be admixed with such epoxy resin compositions when so desired. Various accelerators, extenders and plasticizers heretofore used for the preparation of powder coating compositions are usable.

Uniform and defoamed epoxy resin compositions can be prepared merely by stirring the desired ingredients at room temperature. Such epoxy resin compositions are curable under the conditions usually used for curing epoxy resins. When a suitable curing agent is used in an appropriate amount in accordance with the use of a particular epoxy resin composition, the composition is curable at room temperature to 200° C. The epoxy resin compositions are useful for widespread applications, for example, for adhesion, coating, molding, lining, sealing and potting.

The polycarboxylic acid glycidyl acrylates and/or methacrylates obtained by adducting acrylic acid and/or methacrylic acid with Compounds 2 to 9 of this invention are readily curable with ultraviolet rays, so that the products are advantageously usable for coating compositions and links curable with ultraviolet rays. In addition, Compounds 1 to 9 are useful as curing agents for urethane resins.

Given below are reference examples in which polycarboxylic acids of the formula (I) are prepared as starting materials for preparing present compounds, and examples of this invention in which compounds of the invention are prepared and used. In the following examples, the parts are all by weight.

REFERENCE EXAMPLE 1

Preparation of
7,8-diphenyl-tetradecane-1,14-dicarboxylic acid
(Material Compound 6)

Into a reactor equipped with a stirrer and a condenser are placed 150 kg of anhydrous methanol, 40 kg of cyclohexanone, 40 kg of 35% aqueous solution of hydrogen peroxide, 53 kg of styrene and 1.5 kg of 98% sulfuric acid. The mixture is stirred at 18° to 20° C. for 30 minutes for reaction. While maintaining the reaction mixture at −5° C., 120 kg of finely divided ferrous sulfate (heptahydrate) is added thereto in small portions for reaction. A 18 kg quantity of 60% sulfuric acid is added to the resulting reaction mixture, which is stirred and thereafter allowed to stand, whereby the mixture is separated into an upper layer of a polycarboxylic acid ester and a lower layer of a ferric salt. The acid layer is washed with dilute sulfuric acid and water, and dried to give 80 kg of methyl polycarboxylate. Yield 94.6% (based on the cyclohexanone used).

The lower salt layer is rectified to recover 98 kg of 99% methanol.

The following dimethyl esters are separated from the methyl polycarboxylate by gas chromatography.

(1) Dimethyl-8,9-diphenyl-1,16-hexadecanedioate
(ratio: 60.2%)

| IR: | 700 cm$^{-1}$ |
|---|---|
| | 760 cm$^{-1}$ |
| | 1740 cm$^{-1}$ ($>$C=O) |

| | -continued | |
|---|---|---|
| | 1450 cm$^{-1}$ | $(-\overset{\overset{O}{\|}}{C}-O-)$ |
| NMR: | τ 3.6 | $(-OCH_3)$ |
| | 2.3–1.4 | $(-CH_2-)$ |
| | 3.2–2.8 |  |
| | 7.1 |  |
| | 2.7 |  |
| Hydrogen ratio: | (6:24:2:10:12) | |
| Mass: | 466 (M$^+$) | |
| | 435 (M$^+$ —OCH$_3$) | |
| | 232 (M$^+$/2-H) | |
| | 201 (M$^+$/2-H—OCH$_3$) | |
| Elementary analysis | C (%) | H (%) | O (%) |
| Calcd. for C$_{30}$H$_{42}$O$_4$: | 77.25 | 9.01 | 13.74 |
| Found: | 77.00 | 9.11 | 13.86 |

(2) Dimethyl-7-phenyl-1,14-tetradecanedioate (ratio: 21.7%)

| IR: | 700 cm$^{-1}$ | |
|---|---|---|
| | 760 cm$^{-1}$ | |
| | 1750 cm$^{-1}$ | $(\rangle C=O)$ |
| | 1450 cm$^{-1}$ | $(-\overset{\overset{O}{\|}}{C}-O-)$ |
| NMR: | τ 3.6 | $(-OCH_3)$ |
| | 2.3–1.4 | $(-CH_2-)$ |
| | 7.1 |  |
| | 2.7 |  |
| Hydrogen ratio: | (6:22:1:5:6) | |
| Mass: | 362 (M$^+$) | |
| | 331 (M$^+$—OCH$_3$) | |
| Elementary analysis | C (%) | H (%) | O (%) |
| Calcd. for C$_{22}$H$_{34}$O$_4$: | 79.04 | 10.18 | 19.16 |
| Found: | 79.24 | 10.04 | 18.97 |

The dimethyl dicarboxylates thus obtained are hydrolyzed to obtain Material Compound 6.

REFERENCE EXAMPLE 2

Preparation of tetradecane-1,7,8,14-tetracarboxylic acid (Material Compound 9)

A 50 kg quantity of dimethyl-7,8-dimethyl-1,7,8,14-carboxylic acid ester and 100 kg of water are placed in a reactor equipped with a stirrer, a thermometer and a condenser. The mixture is then heated at 90° C. with stirring and thereto is added 52 kg of 50% aqueous solution of NaOH. Subsequently the resulting mixture is stirred at 95° to 100° C. for 2 hours to undergo saponification. After the completion of the saponification, 66 kg of 50% aqueous solution of sulfuric acid is added to the saponified mixture with stirring to achieve a pH of 3. The heating is discontinued after stirring for 10 minutes. Thereafter the reaction mixture is allowed to stand for about 30 minutes, whereby the mixture is separated into an upper layer and a lower layer. The upper layer is washed with warm water (about 80° C.) three times, heated up to 150° C. at reduced pressure (3 to 5 mmHg) and dried to give 43.1 kg of aliphatic polycarboxylic acid (acid value 649.3, saponification value 650.1, color G2-3).

The aliphatic polycarboxylic acid is subjected to gas chromatography to obtain Material Compound 9.

| IR: | 1750 cm$^{-1}$ ( $\rangle C=O$) | |
|---|---|---|
| | 1450 cm$^{-1}$ $(-\overset{\overset{O}{\|}}{C}-O-)$ | |
| NMR: | τ −2.0 ~ −1.0 (—OH) | |
| | 7.7–8.6 (—CH$_2$—) | |
| | 6.8–7.2 $(-\overset{\overset{\|}{}}{\underset{\underset{H}{\|}}{C}}-)$ | |
| Hydrogen ratio: | (4:24:2) | |
| Mass: | 374 (M$^+$) | |
| Elementary analysis | C (%) | H (%) | O (%) |
| Calcd. for C$_{18}$H$_{30}$O$_8$: | 57.75 | 8.02 | 34.23 |
| Found: | 57.72 | 8.10 | 34.18 |

EXAMPLE 1

Preparation of octadecane-1,18-dicarboxylic acid glycidyl ester (Compound 1)

Octadecane-1,18-dicarboxylic acid (342 parts), 925 parts of epichlorohydrin and 2 parts of benzyltriethyl ammonium chloride are heated and refluxed at 90° to 100° C. for 30 minutes with stirring for esterification. At the same temperature, 208 parts of 50% aqueous solution of sodium hydroxide is added dropwise to the mixture over a period of 60 minutes. The mixture is further heated with stirring for 15 minutes. When the temperature of the mixture has reached 105° C., the mixture is cooled to room temperature and filtered to remove sodium chloride. The epichlorohydrin is recovered from the filtrate in a vacuum, the residue is dissolved in 1 liter of toluene, and the solution is washed with three 300-ml portions of water. The solution is distilled in a vacuum (1 mm Hg) to completely recover the toluene at 140° C. to obtain octadecane-1,18-dicarboxylic acid diglycidyl ester.

Yield 98.4%, epoxy equivalent weight 240, neutralization value 0.02, saponification value 260.1, chlorine content 0.16%, color G1, m.p. 89° C.

EXAMPLE 2

Preparation of 7,11-octadecadiene-1,18-dicarboxylic acid diglycidyl ester (Compound 2)

Into a four-necked flask equipped with a stirrer, a condenser with a water separator, a thermometer and a separating funnel are placed 338 parts of 7,11-octadecadiene-1,18-dicarboxylic acid, 925 parts of epichlorohydrin and 2 parts of benzyltriethyl ammonium chloride. The mixture is heated to 90° to 100° C. and refluxed with stirring for 30 minutes for esterification. At the same temperature, 208 parts of 50% aqueous solution of sodium hydroxide is added dropwise to the mixture over a period of 60 minutes. The mixture is further refluxed with stirring at the same temperature for 15 minutes, then cooled to room temperature and filtered to remove sodium chloride. The epichlorohydrin is recovered in a vacuum, the product is dissolved in 1 liter of toluene, and the solution is washed with three 300-ml portions of water. The solution is distilled in a vacuum (1 mm Hg) to completely recover the toluene at 140° C. to obtain 7,11-octadecadiene-1,18-dicarboxylic acid diglycidyl ester.

Yield 97%, epoxy equivalent weight 240, acid value 0.03, iodine value 108.8, saponification value 233.3, chlorine content 0.31%, color G1, viscosity 83 cps (23° C.).

EXAMPLE 3

Preparation of 6-vinyl-9-hexadecene-1,16-dicarboxylic acid diglycidyl ester (Compound 3)

Compound 3 is prepared in the same manner as in Example 2 except that 338 parts of 6-vinyl-9-hexadecene-1,16-dicarboxylic acid is used.

Yield 96.1%, epoxy equivalent weight 243, acid value 0.03, iodine value 105.1, saponification value 230, chlorine content 0.35%, color G1, viscosity 90 cps (23° C.).

EXAMPLE 4

Preparation of 7,12-dimethyl-7,11-octadecadiene-1,18-dicarboxylic acid diglycidyl ester (Compound 4)

Compound 4 is prepared in the same manner as in Example 2 except that 366 parts of 7,12-dimethyl-7,11-octadecadiene-1,18-dicarboxylic acid is used.

Yield 96.1%, epoxy equivalent weight 270, acid value 0.03, iodine value 98.7, saponification value 215, color G1, viscosity 70 cps (23° C.).

EXAMPLE 5

Preparation of 7,12-dimethyl-octadecane-1,18-dicarboxylic acid diglycidyl ester (Compound 5)

Compound 5 is prepared in the same manner as in Example 2 except that 370 parts of 7,12-dimethyl-octadecane-1,18-dicarboxylic acid is used.

Yield 96.5%, epoxy equivalent weight 265, acid value 0.03, iodine value 0, saponification value 214, color G1, viscosity 65 cps (23° C.).

EXAMPLE 6

Preparation of 7,8-diphenyl-tetradecane-1,14-dicarboxylic acid diglycidyl ester (Compound 6)

Compound 6 is prepared in the same manner as in Example 2 except that 438 parts of 7,8-diphenyltetradecane-1,14-dicarboxylic acid is used.

Yield 97%, epoxy equivalent weight 290, acid value 0.02, iodine value 0, saponification value 195, color G1, viscosity 250 cps (23° C.).

EXAMPLE 7

Preparation of tetradecane-1,6,7,8,9,14-hexacarboxylic acid hexaglycidyl ester (Compound 7)

Compound 7 is prepared in the same manner as in Example 2 except that 462 parts of tetradecane-1,6,7,8,9,14-hexacarboxylic acid is used.

Yield 90.5%, epoxy equivalent weight 150.5, acid value 0.03, iodine value 0, saponification value 372, color G1, viscosity 230 cps (23° C.).

EXAMPLE 8

Preparation of 7,8-dimethyl-tetradecane-1,7,8,14-tetracarboxylic acid tetraglycidyl ester (Compound 8)

Compound 8 is prepared in the same manner as in Example 2 except that 462 parts of 7,8-dimethyl-tetradecane-1,7,8,14-tetracarboxylic acid is used.

Yield 92%, epoxy equivalent weight 172, acid value 0.03, iodine value 0, saponification value 362.2, color G1, viscosity 226 cps (23° C.).

EXAMPLE 9

Preparation of tetradecane-1,7,8,14-tetracarboxylic acid tetraglycidyl ester (Compound 9)

Compound 9 is prepared in the same manner as in Example 2 except that 374 parts of tetradecane-1,7,8,14-tetracarboxylic acid is used.

Yield 92%, epoxy equivalent weight 140.5, acid value 0.03, iodine value 0, saponification value 399.3, color G2, viscosity 191 cps (23° C.).

EXAMPLE 10

Preparation of powder coating composition with use of Compound 1

A powder of the octadecane-1,18-dicarboxylic acid diglycidyl ester obtained in Example 1, dicyandiamide (curing agent), titanium white (pigment) and flow regulator ("Modaflow") are mixed together in the proportions listed in Table 1 below, kneaded with two rolls at 100° C. for 7 minutes, cooled and pulverized to obtain a powder coating composition entirely passing through a 200-mesh screen. The coating composition is applied by an applicator to cold-rolled sheet steel (as specified in JIS G 3141) to a thickness of 150 to 172μ and baked at 180° C. for 30 minutes. For comparison, another coating composition listed in Table 3 is prepared in the same manner as above except that a commercial epoxy resin (trade mark "DER 664," product of Dow Chemical Co.). The coatings obtained are tested for properties with the results also shown in Table 3.

TABLE 3

|  | Example 1 | Comp. Ex. |
|---|---|---|
| Composition | | |

TABLE 3-continued

|  | Example 1 | Comp. Ex. |
|---|---|---|
| Epoxy resin | 100 | 100 |
| Dicyandiamide | 8 | 2 |
| Titanium white | 50 | 50 |
| Modaflow | 1 | 1 |
| Properties |  |  |
| Pencil hardness | 2H | 2H |
| Erichsen penetration value (mm) | 7.5 | 7.7 |
| Impact value (cm) | 45 | 45 |
| Gloss (%) | 89 | 82 |
| Weather resistance | No change | Yellowing |

The properties listed are determined by the following methods.

Pencil hardness: According to JIS K 5400 with use of "UNI" pencils, product of Mitsubishi Pencil Co., Ltd., Japan, under a load of 1 kg.

Erichsen penetration value: According to JIS B 7777 with use of a punch of 20 mm in diameter.

Impact value: Determined according to JIS K 5400 by a Du Pont impact tester, using a 500 g weight of a ½" notch at a falling height of 50 cm.

Gloss: Specular reflectance at a reflection angle of 60°.

Weather resistance: Determined by exposing the coating to outdoor atmosphere at Kashihara-shi, Osaka for one year and thereafter observing the coating surface with the unaided eye.

EXAMPLE 11

Measurement of viscosities of compositions prepared by admixing Compounds 2, 3, 4 and 6 with commercial epoxy resin Each of the compounds of this invention listed in Table 4 is admixed, in the amounts also listed in Table 4, with 100-part portions of bisphenol A type resin (trade mark "Epikote 828," product of Shell Co.) to prepare uniform solutions. The viscosity (in cps) of each resin composition is measured at 25° C. with use of a B-type viscosimeter (product of Tokyo Keiki Co., Ltd., Japan). Table 4 shows the results. For comparison, the same procedure is repeated using the following compounds heretofore known as the best diluents or flexibility imparting agents.

Compound A: phenyl glycidyl ether.

Compound B: Epikote 871 (trade mark for dimer acid glycidyl ester having an epoxy equivalent weight of 430 and manufactured by Shell Co.)

Compound C: SB-20 (trade mark for 6-ethylhexadecane-1,16-dicarboxylic acid diglycidyl ester having an epoxy equivalent weight of 300 and manufactured by Okamura Oil Mill Limited). The results are given also in Table 4.

TABLE 4

| Compound | Amount of test compound (parts) | | | | | | | |
|---|---|---|---|---|---|---|---|---|
|  | 0 | 5 | 10 | 20 | 40 | 50 | 60 | 80 |
| Invention |  |  |  |  |  |  |  |  |
| Comp. 2 | 17000 | 7700 | 2800 | 1800 | 930 | 700 | 530 | 250 |
| Comp. 3 | 17000 | 7500 | 2600 | 1400 | 900 | 650 | 410 | 230 |
| Comp. 4 | 17000 | 4000 | 2400 | 1150 | 650 | 360 | 250 | 145 |
| Comp. 6 | 17000 | 7000 | 4500 | 2400 | 1100 | 850 | 610 | 450 |
| Comparison |  |  |  |  |  |  |  |  |
| Comp. A | 17000 | 11000 | 3500 | 2300 | 1200 | 1000 | 800 | 650 |
| Comp. B | 17000 | 10000 | 8000 | 5000 | 2600 | 2000 | 1400 | 900 |
| Comp. C | 17000 | 8000 | 2900 | 1850 | 1000 | 800 | 600 | 450 |

Table 4 shows that the compounds of the invention have lower viscosities and are more excellent in diluting properties than the comparison compounds.

EXAMPLE 12

Epoxy resin compositions are prepared from Epikote 828 and Compounds 2 to 9 of the invention by uniformly dissolving the ingredients in the proportions listed in Tables 5 and 6. The compositions are allowed to stand at room temperature for 30 days and then checked for formation of crystals and phase separation. Table 5 shows the results. The compositions are also allowed to stand at 0° C. for 7 days and are then similarly checked. Table 6 shows the results. The marks listed in these tables have the following meaning.

O: completely transparent.

Δ: turbid.

X: solid with phase separation or turbidity.

The compositions marked with "O" or "Δ" are usable as epoxy resin compositions.

TABLE 5

| Epikote 828 (parts) | Comp. of invention (parts) | Test compound | | | | | | | | | |
|---|---|---|---|---|---|---|---|---|---|---|---|
|  |  | This invention | | | | | | | | Comp. | |
|  |  | 2 | 3 | 4 | 5 | 6 | 7 | 8 | 9 | B | C |
| 90 | 10 | O | O | O | O | O | O | O | O | O | O |
| 80 | 20 | O | O | O | O | O | O | O | O | O | O |
| 70 | 30 | O | O | O | O | O | O | O | O | Δ | O |
| 60 | 40 | O | O | O | O | O | O | O | O | Δ | O |
| 50 | 50 | Δ | O | O | O | O | O | O | O | X | Δ |
| 40 | 60 | Δ | O | O | O | O | O | O | O | X | Δ |
| 20 | 80 | Δ | Δ | O | O | O | O | O | O | X | X |

TABLE 6

| Epikote 828 (parts) | Comp. of invention (parts) | Test compound | | | | | | | | | |
|---|---|---|---|---|---|---|---|---|---|---|---|
|  |  | This invention | | | | | | | | Comp. | |
|  |  | 2 | 3 | 4 | 5 | 6 | 7 | 8 | 9 | B | C |
| 90 | 10 | O | O | O | O | O | O | O | O | Δ | O |
| 80 | 20 | O | O | O | O | O | O | O | O | Δ | Δ |
| 70 | 30 | O | O | O | O | O | O | O | O | X | Δ |
| 60 | 40 | Δ | O | O | O | O | O | O | O | X | Δ |
| 50 | 50 | Δ | O | O | Δ | O | O | O | O | X | Δ |
| 40 | 60 | Δ | O | O | Δ | O | O | O | O | X | Δ |
| 20 | 80 | X | O | O | X | O | O | O | O | X | X |

Tables 5 and 6 reveal that the compounds of the invention are much more miscible with the epoxy resin than the comparison compounds and that the compositions having the present compounds incorporated therein have higher storage stability especially at a low temperature.

EXAMPLE 13

(1) Preparation of cured product

Epikote 828, a test compound (present compound or comparison compound) and hexahydrophthalic anhydride (hereinafter referred to as "HHPA") are mixed together in the proportions listed in Table 7. The mixture is heated at 80° C. for 2 hours, at 120° C. for 2 hours and at 150° C. for 4 hours to obtain a cured product. Furthermore, Epikote 828, a test compound (present compound or comparison compound), diaminodiphenylmethane (hereinafter referred to as "DDM") are mixed together in the proportions given in Table 8. The mixture is heated at 100° C. for 2 hours and at 150° C. for 2 hours to obtain a cured product.

TABLE 7

| Test compound (parts) | Epikote 828 (parts) | HHPA (parts) |
| --- | --- | --- |
| Comp. 2  20 | 100 | 93.9 |
| Comp. 3  20 | 100 | 94.0 |
| Comp. 4  20 | 100 | 92.3 |
| Comp. 6  20 | 100 | 91.7 |
| None   — | 100 | 81.0 |
| Comp. B  20 | 100 | 88.2 |
| Comp. C  20 | 100 | 91.3 |

TABLE 8

| Test compound (parts) | Epikote 828 (parts) | DDM (parts) |
| --- | --- | --- |
| Comp. 2  20 | 100 | 33.1 |
| Comp. 3  20 | 100 | 30.3 |
| Comp. 4  20 | 100 | 29.7 |
| Comp. 6  20 | 100 | 29.4 |
| None   — | 100 | 26.0 |
| Comp. B  20 | 100 | 28.3 |
| Comp. C  20 | 100 | 29.9 |

(2) Mechanical properties of cured product

According to JIS K 6919, test pieces (80×25×3 mm) are prepared from the cured products obtained above. The test pieces are tested for bending strength and modulus of bending elasticity by a tester "TOM 500" (product of Shinko Tsushin Sha Co., Ltd., Japan) under the conditions of: bending rate 1 mm/min, span 50.8, loading point R 3.17 mm, and temperature 20°±2° C. Dumbbell No. 1 test pieces are also prepared and then tested for tensile strength and elongation with use of the same tester under the conditions of: pulling rate 5 m/min and temperature 20° C. Further test pieces (63.5×12.7 and 12.7 mm) are prepared and then tested for impact strength (Izod impact value) using "UF Impact Tester" (product of Ueshima Mfg. Co., Ltd., Japan) at a temperature of 23° to 25° C., with a V-notch formed in the test piece. Further according to JIS K-6010, the test pieces are tested for Barcol hardness using 934 I type tester at a temperature of 22° to 25° C. Table 9 shows the test results.

Table 9 shows that the epoxy resin compositions containing compounds of this invention are comparable or superior in mechanical properties to those containing the comparison compounds. It is seen that the compositions according to this invention and containing DDM have much higher mechanical strength than the one not containing the present compound or comparison compound.

(3) Thermal impact resistance of cured product

The cured products are tested for resistance to thermal impact by the flat washer method. A flat washer, 20 mm in diameter, is placed in an aluminum cup 50 mm in diameter, as supported on a piece of kraft paper, and one of the epoxy resin compositions listed in Tables 7 and 8 is placed into the cup in an amount of 50 g and then cured under the same conditions as in section (1) above. In this way, five test specimens are prepared for each of the compositions. The specimens are subjected to thermal impact cycles shown in Table 10 to calculate a crack resistance index from the following equation.

Crack resistance index =

$$\frac{\Sigma(\text{Number of cracks produced}) \times \text{Number of cracked specimens}}{\text{Total number of specimens}}$$

Table 11 shows the results.

TABLE 10

| No. | Temp. (°C.) | Time (min) |
| --- | --- | --- |
| 1 | 0 | 10 |
| 2 | 50 | 30 |
| 3 | 0 | 10 |
| 4 | 50 | 30 |
| 5 | 0 | 10 |
| 6 | 75 | 30 |
| 7 | 0 | 10 |
| 8 | 75 | 30 |
| 9 | 0 | 10 |
| 10 | 100 | 30 |
| 11 | 0 | 10 |
| 12 | 100 | 30 |
| 13 | 0 | 10 |
| 14 | 125 | 30 |
| 15 | 0 | 10 |
| 16 | 125 | 30 |
| 17 | 0 | 10 |
| 18 | 150 | 30 |
| 19 | 0 | 10 |
| 20 | 150 | 30 |

TABLE 9

| Test compound | | Bending strength (Kg/mm$^2$) | Modulus of bending elasticity (Kg/mm$^2$) | Tensile strength (Kg/mm$^2$) | Elongation (%) | Izot impact value (Kgcm/cm) | Barcol hardness |
| --- | --- | --- | --- | --- | --- | --- | --- |
| HHPA - cured | Invention  2 | 13.58 ± 0.2 | 324 ± 25 | 7.78 ± 1.9 | 7.7 | 4.3 ± 1.1 | 32 |
|  | 3 | 13.64 ± 0.2 | 331 ± 20 | 7.86 ± 1.6 | 8.0 | 4.5 ± 1.1 | 33 |
|  | 4 | 14.20 ± 0.3 | 328 ± 15 | 7.84 ± 1.0 | 8.5 | 4.7 ± 1.2 | 33 |
|  | 6 | 15.00 ± 0.7 | 331 ± 25 | 8.30 ± 1.2 | 7.7 | 5.2 ± 1.2 | 34 |
|  | Comp. None | 15.10 ± 0.7 | 331 ± 27 | 8.60 ± 1.0 | — | 3.7 ± 4.5 | 35 |
|  | B | 13.55 ± 1.1 | 330 ± 22 | 6.63 ± 0.9 | (4.0) | 2.9 ± 1.2 | 30 |
|  | C | 13.73 ± 1.1 | 319 ± 18 | 7.64 ± 1.2 | 7.7 | 4.3 ± 1.5 | 32 |
| DDM - cured | Invention  2 | 13.46 ± 0.2 | 311 ± 33 | 8.22 ± 0.5 | 6.6 | 3.3 ± 0.6 | 30 |
|  | 3 | 13.60 ± 0.4 | 315 ± 27 | 8.35 ± 0.5 | 7.0 | 3.5 ± 1.0 | 30 |
|  | 4 | 14.00 ± 0.2 | 315 ± 10 | 8.38 ± 0.8 | 8.0 | 4.0 ± 1.2 | 29 |
|  | 6 | 14.38 ± 0.2 | 326 ± 20 | 8.12 ± 1.0 | 7.2 | 4.5 ± 1.3 | 32 |
|  | Comp. None | 13.10 ± 1.0 | 293 ± 22 | 7.64 ± 1.5 | 6.4 | 3.5 ± 1.1 | 33 |
|  | B | 9.58 ± 2.2 | 306 ± 5 | 5.20 ± 2.1 | 4.9 | 3.9 ± 1.9 | 29 |
|  | C | 13.11 ± 1.0 | 255 ± 26 | 7.70 ± 1.9 | 6.5 | 2.5 ± 1.3 | 7 |
|  | | 20 | 150 | 30 | | | |

TABLE 11

| Test compound | | | Number of broken specimens (Cycles) | | | | | | | | Crack resistance index |
|---|---|---|---|---|---|---|---|---|---|---|---|
| | | | 0 | 1 | 3 | 5 | 7 | 9 | 11 | 13 | |
| HHPA - cured | Invention | Comp. 2 | 0 | 1 | 1 | 0 | 0 | 0 | 3 | — | 7.4 |
| | | Comp. 3 | 0 | 0 | 0 | 0 | 1 | 1 | 3 | — | 9.8 |
| | | Comp. 4 | 0 | 0 | 0 | 0 | 0 | 0 | 2 | 2 | 11.0 |
| | | Comp. 6 | 0 | 0 | 0 | 0 | 0 | 0 | 0 | 0 | None broken |
| | Comp. | None | 4 | 1 | — | — | — | — | — | — | 0.2 |
| | | Comp. B | 2 | 0 | 2 | 1 | — | — | — | — | 2.2 |
| | | Comp. C | 2 | 2 | 1 | — | — | — | — | — | 1.0 |
| DDM - cured | Invention | Comp. 2 | 4 | 0 | 1 | — | — | — | — | — | 0.6 |
| | | Comp. 3 | 2 | 1 | 1 | — | — | — | — | — | 0.8 |
| | | Comp. 4 | 0 | 0 | 2 | 3 | — | — | — | — | 4.2 |
| | | Comp. 6 | 0 | 0 | 0 | 2 | 1 | 2 | — | — | 7.0 |
| | Comp. | None | 5 | — | — | — | — | — | — | — | 0 |
| | | Comp. B | 5 | — | — | — | — | — | — | — | 0 |
| | | Comp. C | 5 | — | — | — | — | — | — | — | 0 |

Table 11 reveals that when cured with HHPA or DDM, the epoxy resin compositions containing compounds of this invention have much higher thermal impact resistance than the epoxy resin (i.e. Epikote 828).

(4) Resistance to chemicals

Test pieces (25×25×3 mm) prepared from the cured products obtained in section (1) above are immersed in 20% sulfuric acid for 6 days, in 20% sodium hydroxide for 6 days, in toluene for 6 days and boiling water for 4 hours individually, and are thereafter checked for appearance and a change in weight. Table 12 shows the results. The change of weight is calculated from the following equation.

Change of weight =
$$\frac{\text{Weight after test} - \text{Weight before test}}{\text{Weight before test}} \times 100(\%)$$

TABLE 12

| | | | Resistance to | | | | | | | |
|---|---|---|---|---|---|---|---|---|---|---|
| | | | Boiling water | | Sulfuric acid | | NaOH | | Toluene | |
| Test compound | | | Change of weight | Appearance | Change of weight | Appearance | Change of weight | Appearance | Change of weight | Appearance |
| HHPA - cured | Invention | Comp. 2 | 0.5 | No change | 0.1 | No change | 0.1 | No change | 0.2 | No change |
| | | Comp. 3 | 0.7 | No change | 0.1 | No change | 0.2 | No change | 0.2 | No change |
| | | Comp. 4 | 0.6 | No change | 0.1 | No change | 0.1 | No change | 0.1 | No change |
| | | Comp. 6 | 0.2 | No change | 0 | No change | 0.1 | No change | 0 | No change |
| | Comp. | None | 0.6 | No change | 0.1 | No change | 0.1 | No change | 0 | No change |
| | | Comp. B | 0.5 | No change | 0.2 | No change | −0.2 | No change | 0.5 | No change |
| | | Comp. C | 0.4 | No change | 0.1 | No change | 0.1 | No change | 0.2 | No change |
| DDM - cured | Invention | Comp. 2 | 0.6 | No change | 0.1 | Turns green | 0.2 | No change | 0 | No change |
| | | Comp. 3 | 0.7 | No change | 0.2 | Turns green | 0.2 | No change | 0 | No change |
| | | Comp. 4 | 0.6 | No change | 0.1 | Turns green | 0.1 | No change | 0 | No change |
| | | Comp. 6 | 0.4 | No change | 0 | Turns green | 0 | No change | 0 | No change |
| | Comp. | None | 0.7 | No change | 0.1 | Turns green | 0.3 | No change | 0.2 | No change |
| | | Comp. B | 0.7 | No change | 0.3 | Turns green | 0 | No change | −0.1 | No change |
| | | Comp. C | 0.5 | No change | 0.3 | Turns green | 0 | No change | 0 | No change |

Table 12 shows that the cured products of the epoxy resin compositions containing compounds of this invention are comparable to conventional cured products in resistance to chemicals.

(5) Electrical characteristics of cured product

According to JIS K 6911, test pieces (80×25×3 mm) are prepared from the cured products obtained in section (1) above, and tested for volume intrinsic resistivity, surface intrinsic resistivity, dielectric constant, dielectric loss factor, insulation breakdown voltage, tracking resistance and arc resistance at room temperature (23° C.). The tracking resistance is determined by the IEC method, using 0.1% NH$_4$Cl for the electrolyte and applying 600 V across brass electrodes. The results are shown in Table 13.

The dryness and flexural strength listed above are determined by the following methods. The pencil hard-

TABLE 13

| Test compound | | | Volume intrinsic resistivity (Ω/hr) | Surface intrinsic resistivity (Ω/hr) | Dielectric constant (ε) | Dielectric loss factor (%) | Insulation breakdown constant (KV/mm) | Tracking resistance | Arc resistance (sec) |
|---|---|---|---|---|---|---|---|---|---|
| HHPA - cured | Invention | Comp. 2 | $1.1 \times 10^{16}$ | $3.1 \times 10^{15}$ | 3.5 | 0.8 | 29.7 | No change | 148–150 |
| | | 3 | $1.2 \times 10^{16}$ | $3.5 \times 10^{15}$ | 3.4 | 0.8 | 31.8 | " | 146–148 |
| | | 4 | $1.9 \times 10^{16}$ | $7.3 \times 10^{15}$ | 3.3 | 0.6 | 31.0 | " | 148–152 |
| | | 6 | $2.7 \times 10^{16}$ | $7.7 \times 10^{15}$ | 3.3 | 0.4 | 30.4 | " | 142–148 |
| | Comparison | None Comp | $2.9 \times 10^{16}$ | $8.8 \times 10^{15}$ | 3.7 | 1.1 | 29.7 | " | 145–150 |
| | | B | $7.3 \times 10^{15}$ | $3.1 \times 10^{14}$ | 3.8 | 3.6 | 30.2 | " | 132–137 |
| | | C | $1.3 \times 10^{16}$ | $6.5 \times 10^{15}$ | 3.5 | 1.0 | 29.1 | " | 132–136 |
| DDM - cured | Invention | Comp. 2 | $1.0 \times 10^{16}$ | $1.1 \times 10^{16}$ | 4.5 | 0.5 | 31.5 | " | 134–138 |
| | | 3 | $1.0 \times 10^{16}$ | $1.1 \times 10^{16}$ | 4.4 | 0.6 | 30.2 | " | 136–142 |
| | | 4 | $1.7 \times 10^{16}$ | $1.5 \times 10^{16}$ | 4.3 | 0.4 | 30.5 | " | 140–146 |
| | | 6 | $2.6 \times 10^{16}$ | $2.4 \times 10^{16}$ | 4.5 | 0.4 | 29.5 | " | 143–147 |
| | Comparison | None Comp | $2.5 \times 10^{16}$ | $1.8 \times 10^{16}$ | 4.8 | 1.0 | 30.0 | " | 138–143 |
| | | B | $6.8 \times 10^{15}$ | $1.5 \times 10^{16}$ | 4.7 | 1.0 | 29.7 | " | 132–140 |
| | | C | $1.1 \times 10^{16}$ | $2.7 \times 10^{16}$ | 4.6 | 0.8 | 30.1 | " | 129–134 |

*No change occurs when applying 101 drops.

EXAMPLE 14

Preparation of ultraviolet-curable coating compositions with use of Compounds 3, 4, 6 and 7

Compound 3 (100 parts), acrylic acid in an amount of 130% by weight based on the epoxy equivalent weight of the compound, and 1 part of triethylamine and 0.1 part of hydroquinone serving as catalysts are stirred at 100°±20° C. for 2 hours for reaction. The excess of acrylic acid is recovered from the reaction mixture to obtain a polycarboxylic acid glycidyl acrylate.

The acrylate (50 parts), 0.5 part of benzoin isobutyl ether serving as a photosensitizer, 0.1 part of tert-butyl catechol, and 20 parts of toluene are mixed together to obtain a uniform solution as a coating composition which is curable with ultraviolet rays. The composition is applied to a tinplate sheet, 150×150×0.3 mm, to a thickness of 150μ. The coating is then illuminated by a 1-kw mercury lamp spaced apart therefrom by 15 cm, at a wavelength of 365 mm, at 40 w/cm² for 10 minutes.

The same procedure as above is repeated with use of Compounds 4, 6 and 7. Table 14 shows the results.

TABLE 14

| Comp. | Dryness to touch | Pencil hardness | Flexural strength |
|---|---|---|---|
| 3 | Good | 2H | Good |
| 4 | " | " | " |
| 6 | " | " | " |
| 7 | " | " | " | ness is measured in the same manner as in Table 3.
Dryness to touch: According to JIS K 5400.
Flexural strength: According to JIS K 5400, using bending tester at a radius of curvature of 2 mm and bending angle of 180°.

EXAMPLE 15

Heat resistance of Compounds 7, 8 and 9

Compound 7 of the invention, a commercial epoxy resin (Epikote 828), an acid anhydride curing agent (trade mark "HN-2200," product of Hitachi Kasei Co., Ltd., Japan) and 2-ethyl-4-methylimidazole (hereinafter referred to as "EMI") are mixed together in the proportions listed in Table 15 below. The mixture is heated at 80° C. for 2 hours, then at 130° C. for 2 hours and further at 180° C. for 2 hours to obtain a cured product. The product is tested for the properties listed in Table 15.

The same procedure as above is repeated with use of Compounds 8 and 9. The results are given in Table 15.

TABLE 15

| | | Compound 7 | Compound 8 | Compound 9 |
|---|---|---|---|---|
| Composition | Compound | 70 | 70 | 70 |
| | Epikote 828 | 30 | 30 | 30 |
| | HN-2200 | 95 | 85.5 | 99.7 |
| | EMI | 1 | 1 | 1 |
| Property | Bending strength (kg/mm²) | 14.20 | 13.50 | 13.10 |
| | Modulus of bending elasticity (kg/mm²) | 331 | 326 | 318 |
| | Volume intrinsic resistance (Ω/hr.) | $5.7 \times 10^{15}$ | $2.7 \times 10^{15}$ | $10 \times 10^{15}$ |
| | Glass transition temperature(°C.) | 196 | 180 | 198 |
| | Ignition loss (%) | 4.5 | 4.8 | 5.0 |

The properties listed are determined by the following methods.
Grass transition temperature: According to JIS K 6919, Dumbbell No. 1 test pieces are prepared, which are tested by Torsion Pendulum Analyzer at a frequency of 3 Hz while raising the temperature at a rate of 10° C./min.

Volume intrinsic resistivity: Test pieces (80×25×3 mm) prepared according to JIS K 6911 are tested at 23° C.

Ignition loss: Test pieces (10×10×1 mm) is heated at 200° C. for 1,000 hours, and the resulting reduction in weight is measured.

We claim:

1. A polycarboxylic acid glycidyl ester represented by the formula

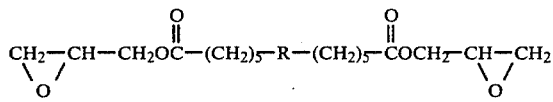

wherein —R— is

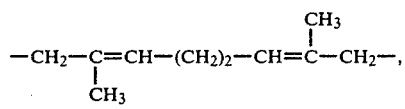

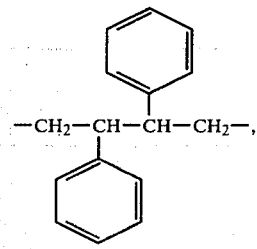

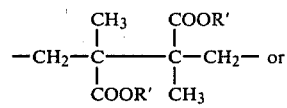

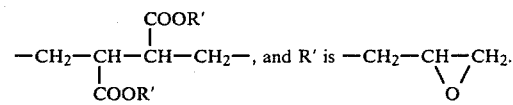

2. A polycarboxylic acid glycidyl ester represented by the formula

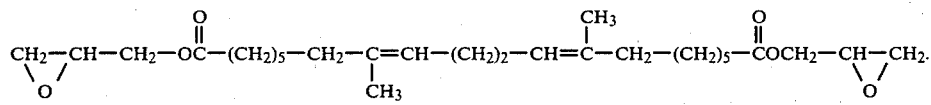

3. A polycarboxylic acid glycidyl ester represented by the formula

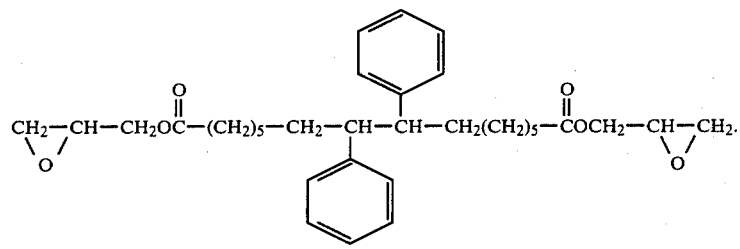

4. A polycarboxylic acid glycidyl ester represented by the formula

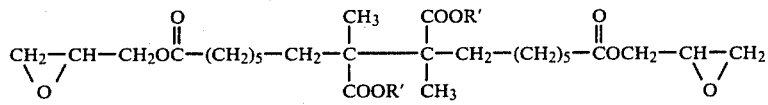

wherein R' is —CH₂—CH—CH₂.

5. A polycarboxylic acid glycidyl ester represented by the formula

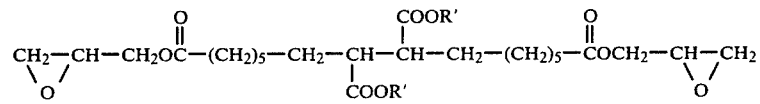

wherein R' is

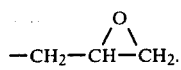

* * * * *